(12) United States Patent
Daburger et al.

(10) Patent No.: US 8,383,181 B2
(45) Date of Patent: Feb. 26, 2013

(54) METHOD AND DEVICE FOR CREMA PRODUCTION BASED ON VOLUMETRIC FLOW

(75) Inventors: Josef Daburger, Siegsdorf-Hammer (DE); Ulrike Gerl, Traunstein (DE); Marijana Jerance Mitrovic, Oxford (GB)

(73) Assignee: BSH Bosch und Siemens Hausgeraete GmbH, Munich (DE)

( * ) Notice: Subject to any disclaimer, the term of this patent is extended or adjusted under 35 U.S.C. 154(b) by 57 days.

(21) Appl. No.: 12/996,631

(22) PCT Filed: Jun. 8, 2009

(86) PCT No.: PCT/EP2009/056997
§ 371 (c)(1),
(2), (4) Date: Dec. 7, 2010

(87) PCT Pub. No.: WO2009/150112
PCT Pub. Date: Dec. 17, 2009

(65) Prior Publication Data
US 2011/0223309 A1 Sep. 15, 2011

(51) Int. Cl.
*A23F 5/26* (2006.01)
(52) U.S. Cl. .............. 426/433; 426/87; 426/77; 99/283; 99/295; 99/289 R; 99/323.1
(58) Field of Classification Search ................. 426/433, 426/82, 77; 99/295, 323.1
See application file for complete search history.

(56) References Cited

U.S. PATENT DOCUMENTS

| 6,698,333 | B2 * | 3/2004 | Halliday et al. ................ 99/295 |
| 7,878,108 | B2 | 2/2011 | Mock et al. |
| 2007/0261564 | A1 | 11/2007 | Suggi Liverani et al. |
| 2009/0013875 | A1 | 1/2009 | Widanagamage Don |
| 2009/0136639 | A1 | 5/2009 | Doglioni Majer |

FOREIGN PATENT DOCUMENTS

| EP | 0486434 A1 | 11/1991 |
| EP | 1440644 A1 | 7/2004 |
| JP | 2003024703 A | 1/2003 |
| WO | 2008078989 A1 | 7/2008 |

OTHER PUBLICATIONS

Report of Examination EP 09 761 675.9.
Report of Examination DE 10 2008 028 031.3.

* cited by examiner

*Primary Examiner* — Anthony Weier
(74) *Attorney, Agent, or Firm* — James E. Howard; Andre Pallapies

(57) ABSTRACT

A method for producing crema in a coffee vending machine that has a flow-through heater for heating water and that is charged with substrate capsules which include a Venturi nozzle for crema production. The method includes a) heating the water in the flow-through heater; b) brewing ground coffee using the heated water in a brewing chamber in order to produce a coffee drink; and c) producing crema by mixing the coffee drink with a gas in the Venturi nozzle. In step c), at least one of two volumetric flows of the coffee drink or the gas is increased in the Venturi nozzle during a predetermined time interval.

16 Claims, 2 Drawing Sheets

METHOD AND DEVICE FOR CREMA PRODUCTION BASED ON VOLUMETRIC FLOW

BACKGROUND OF THE INVENTION

The invention relates to a method for producing crema in a coffee vending machine which comprises a flow-through heater for heating water and which can be charged with substrate capsules comprising a Venturi nozzle for crema production, said method comprising the following continuously executed steps:

heating the water in the flow-through heater brewing the ground coffee using the heated water in a brewing chamber in order to produce a coffee drink and producing crema by mixing the coffee drink with a gas in the Venturi nozzle.

The invention furthermore relates to a corresponding device for carrying out this method.

Coffee drinks, espressos in particular, have a light fine foam, the so-called crema, formed on their surface as a result of the high pressure of between 2 and 10 bar under which they are produced. If coffee drinks are produced under lower pressure however, typically at approximately 1 bar, the pressure based physicochemical processes involved in espresso production do not occur. Although a foam can form, as a rule this has neither a fine bubble structure nor a lasting character however. In order nevertheless to obtain a crema having a fine bubble structure, the coffee drink can among other things be directed through a Venturi nozzle. In said Venturi nozzle the bubble size of the foam can be set relatively exactly and as homogeneous a size distribution of the foam bubbles as possible can be achieved. The crema thus produced is furthermore also very stable, or firm. The relevant parameters for the crema production in a Venturi nozzle are on the one hand the flow rate of the coffee drink through the nozzle and on the other hand the cross-section of the hole through which a gas, ambient air as a rule, is drawn in in order to form the foam. Both the flow rate and also the hole diameter determine the quantity of gas blown in.

A multiple-drink vending machine is on the market which can be charged with drink substrate capsules and with which coffee can also be produced in addition to tea, drinking chocolate and even soups. Since as a rule no foam production is desired for the other drinks, the Venturi nozzle required for the crema production is arranged not at the machine end but in the capsule. In order to improve the crema formation at the machine end it is not therefore possible to fall back on the dimensioning of the Venturi nozzle.

BRIEF SUMMARY OF THE INVENTION

The object of the invention is therefore to specify a method and a device of the type described in the introduction, whereby an improved crema formation can be achieved.

This object is achieved according to the invention by the fact that at least one of the two volumetric flows, in other words that of the coffee drink or of the gas, is increased in the Venturi nozzle for the duration of a particular time interval. The invention thus departs from the obvious approach to a solution by means of varying the dimensioning of the Venturi nozzle at the machine end in order to improve the crema formation. Rather, it follows the principle of influencing the volumetric flows, namely increasing them, to provide improved crema formation without varying the Venturi nozzle. Either it is possible to increase the gas or air supply in the existing flow of the coffee drink, as a result of which the proportion of crema formed increases, or it is possible to increase the volumetric flow of the coffee drink. The invention then skillfully utilizes the already known principles of the Venturi nozzle, according to which an increased flow rate or an increased volumetric flow of the fluid through the Venturi nozzle results in an increased intake of gas. As the volumetric flow of the coffee drink is increased, so too therefore at the same time is that of the gas flow in the Venturi nozzle.

A lasting increase in the volumetric flow or flows would be accompanied by various disadvantages. An increase in the coffee flow also signifies a faster flow rate through the flow-through heater at the same time. In this situation there is a danger that if the design of the drink vending machine is otherwise unchanged the water used for drink preparation is not adequately heated on account of spending too little time in the flow-through heater and the coffee drink dispensed therefore has a lower temperature. The increase in the volumetric flow through the Venturi nozzle can therefore be temporally restricted such that any reduction in heat absorption by the water has no effect as regards taste but a better crema or more crema is produced. According to an advantageous embodiment of the invention, the duration of the time interval can be determined depending on volumetric flow, in other words according to the water quantity delivered. Since a flow meter for measuring a cup portion is in any case present in the preparation device, no appreciable additional technical resources are required for this purpose.

According to a further advantageous embodiment of the invention, the duration of the time interval can be preset at the machine end. This simplifies the operation of the preparation device because a user of the device need pay no attention to an additional setting which may appear to the user as not entirely comprehensible.

According to an alternative form of embodiment of the invention with respect to the above, the time interval can be set manually by a user. By this means the user is given a greater freedom of choice and can adjust the coffee drink individually to suit his taste and his wishes for more or less crema.

The timing of the volumetric flow increase can be of importance both for the result of the crema production and also for the flavor of the prepared coffee drink. According to a further advantageous embodiment of the invention, the increase in the at least one volumetric flow can therefore take place at the end of a cup preparation operation. This has the advantage that the crema is added to the otherwise finished drink towards the end of the preparation operation, with the result that the crema is not destroyed again by the following drink. This form of embodiment can lead to taste-related effects due to the fact that the preparation of the coffee drink in respect of the flow rate of the water at least through the flow-through heater can be set optimally for brewing the drink. This is because the undisturbed ideal brewing in a first preparation phase for a cup portion achieves the taste-related character of the drink as is generally preferred in central Europe. An acceleration of the volumetric flow in order to benefit the crema formation only at the end of the cup preparation operation therefore has minor taste-related effects compared with the current preparation method.

According to an alternative form of embodiment of the inventive method with respect to the above, the increase in the at least one volumetric flow can take place at the beginning of a cup preparation operation. This alternative has the advantage of a particularly stable crema because a particularly large number of foaming agents are dissolved out of the coffee extract at the beginning of the elution process. As a result, a more stable foam can be generated which is also not destroyed to any appreciable extent by following coffee drink.

Basically, either the gas flow or the coffee flow in the Venturi nozzle can be increased. According to a further advantageous embodiment of the invention, the delivery capacity for the water can be increased beyond an optimum capacity at which the water would be heated to the requisite brewing temperature in the flow-through heater. With the increase in the delivery capacity for the water, with which more coffee drink is transported at the same time through the Venturi nozzle, the gas flow of the gas sucked in, ambient air as a rule, is also increased. With this method, the preparation device can essentially remain technically unchanged. The delivery capacity of the pump merely needs to be raised for a certain time interval, for example by increasing the timing of a reciprocating piston pump. In particular, the heating output of the through-flow heater does not need to be increased.

According to a further advantageous embodiment of the invention, the flow-through heater can be preheated, without water having already been delivered, prior to each cup portion being prepared. By this means it is possible to compensate for the lack of heat input into the water which can occur in the case of an accelerated delivery of water for the purpose of crema production as a result of the reduced time spent by the water in the flow-through heater. It is thus possible to lessen a negative effect of crema production on the temperature of the coffee drink.

According to a further advantageous embodiment of the invention, gas can additionally be introduced when the coffee drink is passing through the Venturi nozzle. This action can be taken alone or in addition to increasing the volumetric flow of the coffee drink. This means that an improved crema formation can be achieved without the remainder of the coffee preparation process being affected for example in respect of flow rate and temperature of the coffee drink. The crema production can thus take place almost completely independently of the preparation of a cup portion.

The stated object of the invention can be achieved in the case of the coffee vending machine mentioned in the introduction for coffee preparation using substrate capsules which can be introduced into a brewing chamber and comprise a Venturi nozzle for supplying gas for the purpose of crema production, and which comprises a flow-through heater for heating water to brewing temperature and a pump for transporting the water from the flow-through heater into the brewing chamber, by the fact that it comprises a device for increasing at least one of the two volumetric flows of coffee drink or gas in the Venturi nozzle for the duration of a certain time interval. The invention thus follows the principle of influencing or improving the crema formation without varying the Venturi nozzle. According to the invention, this is done at the machine end, such that no change needs to be made to the capsule.

According to an advantageous embodiment of the drink vending machine, it is possible to determine the time interval dependent on volumetric flow. No additional technical facilities are required for this because a flow meter is in any case present in the coffee vending machine in order to determine the quantity for a cup portion. The determination of the duration of the time interval for which the volumetric flow is increased thus does not signify any additional technical resources and thus no additional costs.

The duration of the time interval can be preset at the machine end. According to a further advantageous embodiment of the invention, the duration of the time interval can be determined manually. The user of the coffee vending machine can thus be offered a choice for adjusting his coffee drink individually to suit his preferences and his taste. The drink vending machine thereby gains an attractive additional function.

According to a further advantageous embodiment of the invention, the coffee vending machine can have a control facility. With this device, the delivery capacity of the pump can be increased for the certain period of time beyond an optimum capacity at which the water would be heated to the requisite brewing temperature. In other words, the control facility switches the pump to a higher capacity at the requisite time and for the requisite time interval. With regard to a determination of the time interval based on volumetric flow, said control facility receives and processes signals from a flow meter which is in any case required for measuring a cup portion. With regard to a purely time-based control mode, said control facility can process signals from a separate timing element.

With regard to this form of embodiment, the volumetric flow of the coffee drink through the Venturi nozzle is thus increased. In accordance with the physical laws of the Venturi nozzle, the gas flow which is sucked in by the fluid flow of the coffee drink is also increased thereby. By means of this form of embodiment of the invention, the crema formation of the drink vending machine can thus be improved without having to implement major technical changes in respect of the performance of the individual components, in particular of the heater or of the Venturi nozzle. The pump merely needs to be designed for a temporary increase in capacity, for example for a temporarily increased timing of a reciprocating piston pump.

The volumetric flow of the coffee drink in the Venturi nozzle is virtually identical to the volumetric flow of the water in the heating facility because both volumetric flows are delivered by the same pump. The water flow is set to an optimum dwell time of the water in the flow-through heater which is required in order to heat it for preparing the coffee drink. An increase in the volumetric flow in the Venturi nozzle is thus also accompanied by an increase in the volumetric flow in the flow-through heater. This means that the dwell time of the water in the flow-through heater is shortened and its energy absorption is consequently reduced. The water is thus heated less. Therefore, according to a further advantageous embodiment of the invention, the control facility can be designed such that the flow-through heater is preheated prior to each cup portion being prepared without water already being present in the flow-through heater. By this means it is possible to almost compensate for an otherwise reduced energy absorption resulting from the greater through-flow rate to provide improved crema production.

According to an alternative form of embodiment of the invention with respect to the above, the drink vending machine can have a delivery facility for the gas feed. Although this constitutes an additional technical resource, it does however have the decisive advantage that the technical equipment of the drink vending machine can otherwise remain unchanged. Therefore there need be no concern about any influencing of the brewing operation in particular with taste-related effects. The gas feed can moreover be controlled completely independently of the remaining drink preparation operation, whereby it is ideally suited to a separate manual setting. The user can thus adjust the crema production to suit his wishes in an extremely convenient manner without having to accept taste-related or temperature-related disadvantages for his drink. The delivery facility for the gas feed can for example comprise an additional pump for ambient air or be supplied from cartridges containing compressed gas or carbon dioxide, which are already available on the market for other applications.

BRIEF DESCRIPTION OF THE DRAWINGS

The principle of the invention will be described in detail in the following with reference to a drawing by way of example. In the drawing.

DETAILED DESCRIPTION OF EXEMPLARY EMBODIMENTS OF THE PRESENT INVENTION

Figure 1:
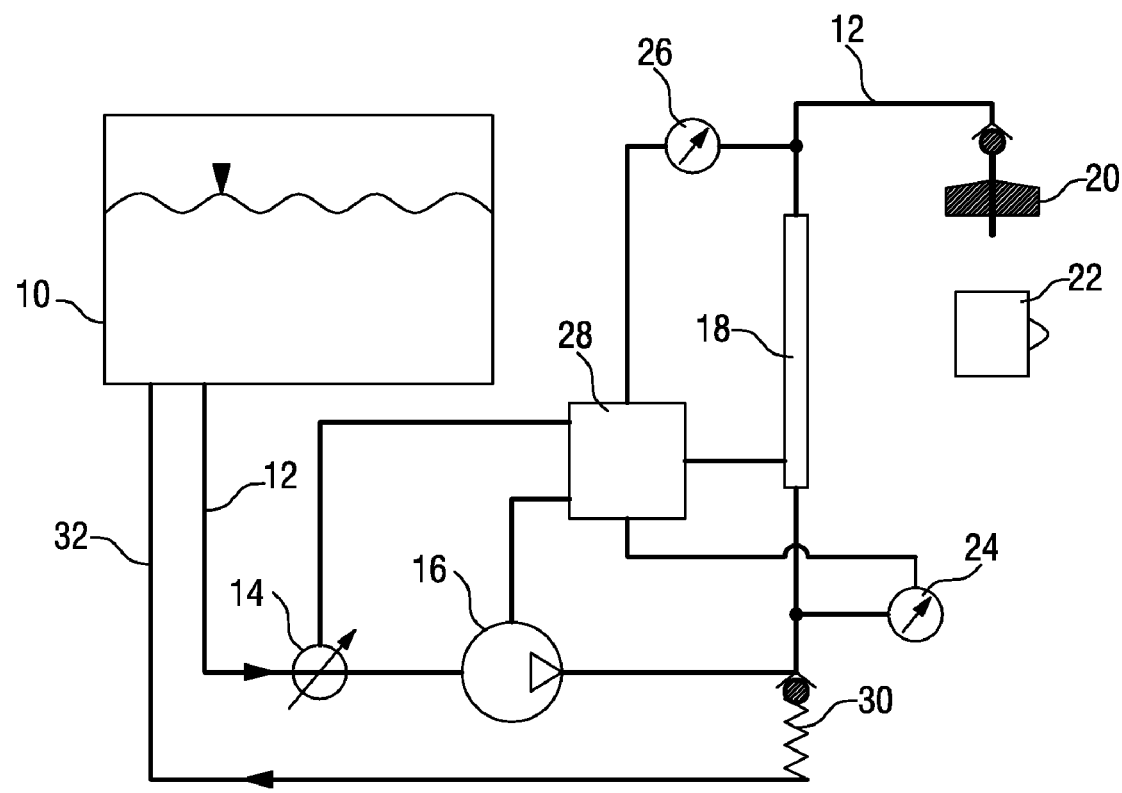
FIG. 1: shows a schematic structure of a coffee making machine.

FIG. 1 schematically illustrates the main component parts of a coffee making machine. A line 12 runs from a fresh water tank 10 to a flow meter 14, which is further connected by way of the line 12 to a pump 16 and a flow-through heater 18 as a heating facility. Downstream of the through-flow heater 18 the line 12 leads to a brewing chamber 20, into which a drink capsule (not shown) having a Venturi nozzle can be introduced. The drink prepared there passes into a cup 22 downstream of the brewing chamber 20. Temperature sensors 24, 26 which sense the water temperature on the input side and output side respectively of the through-flow heater 18 are arranged upstream and downstream respectively of the through-flow heater 18. The temperature sensors 24, 26 and also the pump 16 and the flow meter 14 are connected electrically to a control facility 28. This receives and processes signals from the flow meter 14 and the temperature sensors 24, 26 and controls the pump 16 and the flow-through heater 18. A pressure relief valve 30, which feeds overpressure back into the fresh water tank 10 by way of a pressure relief line 32, is arranged between the pump 16 and the temperature sensor 24.

In order to prepare a coffee drink, the pump 16 continuously delivers fresh water from the water tank 10 by way of the line 12 into the flow-through heater 18. As a result of further fresh water flowing in, the water heated there passes into the brewing chamber 20. There it is injected into a capsule containing drink concentrate or coffee powder and brewed to make a coffee drink. At the outlet from the capsule the coffee drink flows through a Venturi nozzle, in which it sucks in and is mixed with ambient air. The coffee drink is dispensed into the cup 22 and forms a fine crema on its surface.

Figure 2:
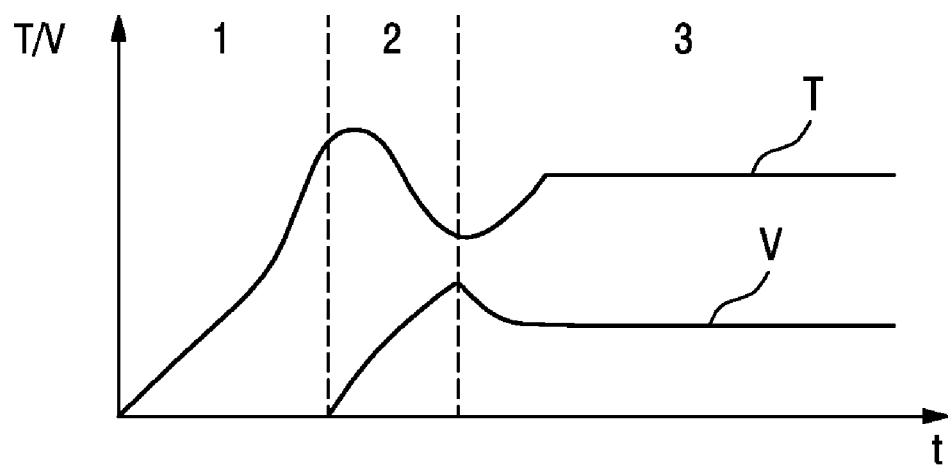
FIG. 2: shows a temperature profile and a delivery profile according to a first control option.
Figure 3:
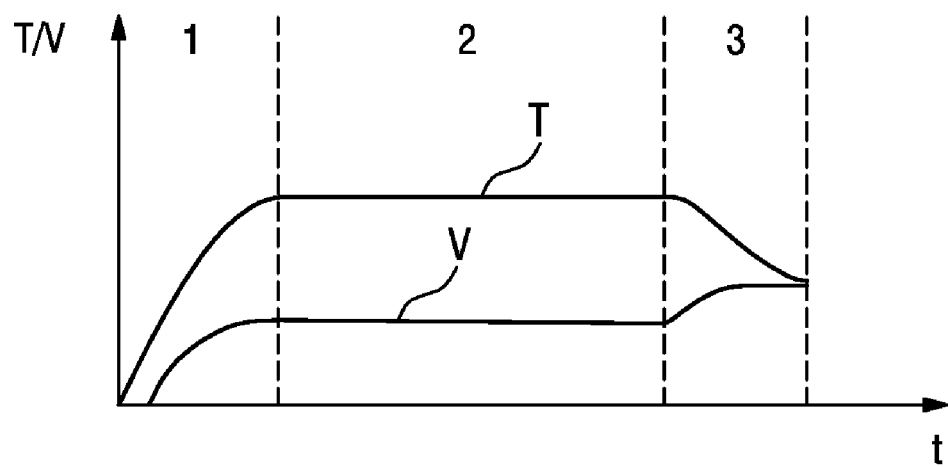
FIG. 3: shows the profiles according to a second control option.

With the control facility 28, the present coffee machine has a device by means of which the volumetric flow of the coffee drink through the Venturi nozzle can be increased in order to produce better or more crema without making changes to the Venturi nozzle itself. The temporally restricted increase in the volumetric flow can basically be carried out at any desired point in time during the entire preparation operation. FIGS. 2 and 3 qualitatively illustrate two profiles for the temperature T and the volumetric flow V during the time t for an increase in the volumetric flow V of the water at the beginning of the preparation operation (FIG. 2) and at the end thereof (FIG. 3).

In the case of an increase in the volumetric flow V at the beginning of the preparation operation according to FIG. 2, after the drink vending machine has been switched on or after a cup portion has been requested the control facility 28 does not as hitherto actuate the pump 16 more or less immediately but first preheats the flow-through heater 18 in a phase 1. Only in a following phase 2 does the control facility 28 put the pump 16 into operation. In this situation, the latter's delivery capacity is initially measured such that the water quantity delivered would not be heated sufficiently for correct drink preparation in a non-preheated flow-through heater 18. The heat input which in itself is too little as a result is at least partially compensated for by the preheating of the through-flow heater 18 in phase 1.

On account of the high flow rate of the fresh water through the flow-through heater 18, the temperature of the fresh water falls during phase 2 compared with its normal operating temperature during a preparation operation. In phase 2, because of the increased flow rate of the fresh water or of the coffee drink through the Venturi nozzle, a particularly large quantity of fine-bubble crema is produced. This is furthermore particularly stable and lasting because surface active molecules are extracted in particularly concentrated fashion from the coffee powder in the drink capsule at the beginning of coffee extraction.

After a certain delivery volume, for example after a pump output of 50 ml, the delivery rate is reduced in a phase 3 to a normal level which is suitable for optimum drink preparation. As a result of the lower flow rate of fresh water through the flow-through heater 18, its temperature rises again to the preparation temperature for a coffee drink. In phase 3, the remaining coffee drink is then prepared under the normal conditions now prevailing, until a cup portion has been prepared.

FIG. 3 shows an alternative control option. According to this, in the conventional manner, firstly in a phase 1 after the drink vending machine has been switched on or after a cup portion has been requested the flow-through heater 18 and a little later also the pump 16 are switched on in order to provide brewing water for preparing the drink. In phase 2, both the delivery rate and also the temperature of the through-flow heater 18 reflect the optimum preparation conditions. The main part of the cup portion is therefore produced in this phase.

In a final phase 3, the control facility 28 increases the output of the pump 16, such that as a result of the now higher water flow rate through the heater 18 the water temperature drops slightly. The greater pump output allows the finished coffee drink to flow at an increased rate through the Venturi nozzle and there to suck in added ambient air. Only in phase 3 does the production of enhanced fine-bubble crema therefore take place, which is poured on the surface of a cup portion after completion of the actual preparation operation. Since this step represents the conclusion of the preparation operation, the crema cannot be destroyed again by further following coffee drink. This control option furthermore represents only a slight modification compared with a conventional control mode of the drink vending machine. In particular, the phases 1 and 2 relevant to flavor at the beginning of the preparation operation are unchanged or undisturbed. The resulting flavor is therefore virtually unaffected by this method of preparing crema.

The last described preparation method thus has the greatest similarity to the conventional preparation method in keeping with central European coffee tastes. However, the first method variant also has its justification if the emphasis is rather on increased crema formation or if the sharper flavor achieved thereby is preferred.

LIST OF REFERENCE CHARACTERS

10 Fresh water tank
12 Fluid line

14 Flow meter
16 Pump
18 Flow-through heater
20 Brewing chamber with capsule and Venturi nozzle
22 Cup
24, 26 Temperature sensor
28 Control facility
30 Pressure relief valve
32 Pressure relief line
T Temperature
V Volume flow

The invention claimed is:

1. A method for producing crema in a coffee vending machine that has a flow-through heater for heating water and that is charged with substrate capsules including a Venturi nozzle for crema production, the method comprising:
   a) heating the water in the flow-through heater;
   b) brewing ground coffee using the heated water in a brewing chamber in order to produce a coffee drink; and
   c) producing crema by mixing the coffee drink with a gas in the Venturi nozzle;
   wherein, in step c), at least one of (i) the volumetric flow of the coffee drink or (ii) the volumetric flow of the gas is increased in the Venturi nozzle for the duration of a predetermined time interval, the predetermined time interval being controlled depending on said volumetric flow of the coffee drink or said volumetric flow of the gas which has been increased.

2. The method of claim 1, wherein the predetermined time interval is set manually.

3. The method of claim 1, wherein the increase in the at least one of the two volumetric flows takes place at the end of a cup preparation operation.

4. The method of claim 1, wherein the increase in the at least one of the two volumetric flows takes place at the beginning of a cup preparation operation.

5. The method of claim 1, wherein a delivery capacity for the water is increased beyond an optimum capacity at which the water would be heated to a requisite brewing temperature in the flow-through heater.

6. The method of claim 5, wherein the flow-through heater is preheated at the beginning of an operation to prepare a cup portion prior to a delivery of the water for heating in step a).

7. The method of claim 1, wherein the gas is additionally introduced when the coffee drink is passing through the Venturi nozzle in step c).

8. A coffee vending machine for coffee preparation using substrate capsules that are introduced into a brewing chamber and that include a Venturi nozzle to supply gas for crema production, the coffee vending machine comprising:
   a flow-through heater to heat water to a brewing temperature;
   a storage tank;
   a pump to transport the water from the storage tank by way of the flow-through heater into the brewing chamber; and
   a control facility configured to control the flow-through heater and the pump which thereby enables a delivery capacity of the pump to be increased for a predetermined period of time beyond an optimum capacity at which the water is heated to a requisite brewing temperature and also increases at least one of two volumetric flows of a coffee drink and the gas in the Venturi nozzle for the duration of a predetermined time interval.

9. The coffee vending machine of claim 8, wherein the predetermined time interval is determined dependent on volumetric flow.

10. The coffee vending machine of claim 8, wherein the predetermined time interval is determined manually.

11. The coffee vending machine of claim 8, further comprising a delivery facility for feeding the gas.

12. A method for producing a coffee drink having crema in a machine that is charged with substrate capsules, the method comprising:
   a) producing the crema by increasing a volumetric flow rate of the coffee drink through the Venturi nozzle for the duration of a predetermined time interval; and
   b) reducing the volumetric flow rate of the coffee drink through the Venturi nozzle after the predetermined time interval,
   wherein the predetermined time interval is controlled depending on the volumetric flow.

13. A method for producing a coffee drink having crema in a machine having a flow-through heater for heating water and that is charged with a substrate capsule including a Venturi nozzle, and a pump to transport the water by way of the flow-through heater to the Venturi nozzle, the method comprising:
   a) delivering water to the Venturi nozzle at a first, increased volumetric flow rate for a first predetermined time interval based on the volumetric flow of the water;
   b) delivering water, after the first predetermined time interval, to the Venturi nozzle for a second predetermined time interval based on the volumetric flow of the water; and
   c) producing crema, after the second predetermined time interval, by delivering water to the Venturi nozzle at a second, increased volumetric flow rate for a third predetermined time interval based on the volumetric flow of the water.

14. The method of claim 13, wherein the second volumetric flow rate is greater than the first volumetric flow rate.

15. The method of claim 13, wherein the second predetermined time interval is greater than the first predetermined time interval and the second predetermined time interval.

16. A coffee vending machine for producing a coffee drink using water and a substrate capsule that includes a Venturi nozzle to supply gas for crema production, the coffee vending machine comprising:
   a brewing chamber to receive the substrate capsule;
   a flow-through heater to heat the water to a brewing temperature;
   a pump to transport the through the flow-through heater and into the brewing chamber;
   a flow meter to measure volumetric flow of the water; and
   a control facility to control the pump based on the measured volumetric flow and increase at least one of two volumetric flows of a coffee drink and the gas in the Venturi nozzle for the duration of the predetermined time interval.

* * * * *

UNITED STATES PATENT AND TRADEMARK OFFICE
CERTIFICATE OF CORRECTION

PATENT NO. : 8,383,181 B2
APPLICATION NO. : 12/996631
DATED : February 26, 2013
INVENTOR(S) : Josef Daburger et al.

Page 1 of 1

It is certified that error appears in the above-identified patent and that said Letters Patent is hereby corrected as shown below:

Title Page, please insert;

-- (30) Foreign Application Priority Data
June 12, 2008   (DE).....10 2008 028 031.3 --

Signed and Sealed this
Seventh Day of May, 2013

Teresa Stanek Rea
*Acting Director of the United States Patent and Trademark Office*

UNITED STATES PATENT AND TRADEMARK OFFICE
CERTIFICATE OF CORRECTION

PATENT NO.       : 8,383,181 B2
APPLICATION NO.  : 12/996631
DATED            : February 26, 2013
INVENTOR(S)      : Daburger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 96 days.

Signed and Sealed this
First Day of September, 2015

Michelle K. Lee
*Director of the United States Patent and Trademark Office*